United States Patent [19]

Ariyoshi et al.

[11] 3,966,485

[45] June 29, 1976

[54] NOVEL RESINS AND MANUFACTURING THE SAME

[75] Inventors: Junji Ariyoshi, Hirakata; Noboru Kariya, Sakai, both of Japan

[73] Assignees: Arakawa Rinsan Kagaku Kogyo Kaisha; Nard Institute, both of Osaka, Japan

[22] Filed: June 23, 1975

[21] Appl. No.: 589,014

Related U.S. Application Data

[62] Division of Ser. No. 296,780, Oct. 12, 1972, abandoned.

[30] Foreign Application Priority Data

Oct. 13, 1971  Japan.............................. 46-80794
Oct. 21, 1971  Japan.............................. 46-83774

[52] U.S. Cl............................ 106/287 R; 162/158; 162/168 R; 260/464; 260/468 G; 260/469; 260/514; 260/515 R; 260/557 B

[51] Int. Cl.²................. C07C 61/12; C07C 63/52; C07G 17/00

[58] Field of Search.............. 106/287 R; 260/514 G

[56] References Cited
UNITED STATES PATENTS 2,608,550  8/1952  Rowland ...................... 260/78.5 R

*Primary Examiner*—Theodore Morris
*Attorney, Agent, or Firm*—Bierman & Bierman

[57] ABSTRACT

A resin having a formula of

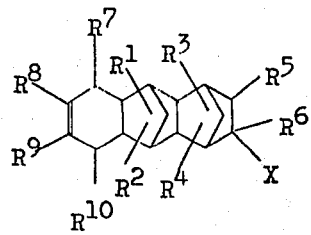

wherein each of $R^1$, $R^2$, $R^3$, $R^4$, $R^5$ and $R^6$ is hydrogen or methyl group, each of $R^7$, $R^8$, $R^9$ and $R^{10}$ is hydrogen, alkyl group having 1 to 6 carbon atoms or phenyl group and X is $-CN$, $-CONH_2$, $-COOM$ or $-COOR^a$, M being hydrogen, $-NH_4$ or alkali metal, $R^a$ being alkyl group having 1 to 4 carbon atoms; and a method for manufacturing the same, said resin being usable as substitutes for rosin and its derivatives.

4 Claims, 6 Drawing Figures

NOVEL RESINS AND MANUFACTURING THE SAME

This application is a division of Ser. No. 296,780 now abandoned, filed Oct. 12, 1972 which in turn claims the priority of Japanese applications 80794/71 and 83774/71, filed Oct. 13 and Oct. 21, 1971, respectively.

This invention relates to a novel resin and manufacturing the same, more particularly to a novel resin usable as substitutes for rosin as well as for derivatives thereof and a process for producing the same. The present invention further pertains to a composition containing the novel resin, which is especially useful as emulsifying agent for producing synthetic rubber by emulsion polymerization and as sizing agent for paper.

As already known, rosin comprises resin acids including abietic acid represented by the formula of

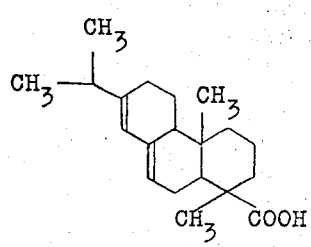

and structural isomers thereof. Because the alkali salt of the resin acid exhibits an excellent surface activity of the anion type and is moreover in the form of a resinous substance having alicyclic structure including unsaturated carbon-carbon bond and carboxyl group, it not only gives more surface activity but also materially improves the quality of industrial materials such as other resins, rubbers, fibers and the like when incorporated therein. For instance, when an alkali salt of rosin is used as an emulsifying agent for the emulsion polymerization to produce styrene-butadiene rubber (SBR) or acrylonitrilebutadiene rubber (NBR), rosin gets incorporated in SBR or NBR to enhance the amenability of the resulting product to processing, giving a tackifying effect to the same. The alkali salt is therefore used universally for industrial purposes. Before application to such uses, the rosin is pretreated to stabilize the conjugated double bond in the molecule by disproportionation reaction in order that the rosin will not inhibit radical polymerization.

In paper making process, an alkali salt of rosin is added to pulp prior to sheet forming step in an amount of 0.1 to 2 wt.% based on the pulp to obtain sized paper which is free of feathering when written on in water-based ink. The size gives much greater effect than other similar surface active agents such as alkali salts of fatty acid of beef tallow and fatty acid of soybean oil. For industrial purposes, fortified rosin sizes are extensively used which are prepared by reacting maleic acid with part of rosin through addition reaction, followed by conversion to alkali salt.

Rosin is soluble in various solvents and has good compatibility with various high molecular weight substances. Rosin is lowest in molecular weight of all resins. Whereas rosin has a molecular weight of about 300, resins having similar softening point to that of rosin (70° to 80°C) generally has a molecular weight of at least 500, mostly a molecular weight of 1,000 to 3,000. For this reason, rosin displays better compatibility with a wider variety of high molecular weight substances than in the case of other resins and, because it is a resin, it gives peculiar effect as distinct from the effect achieved by the use of oily substances. For instance, when incorporated in resin or rubber, oily substances chiefly produce a plasticizing effect while resinous substances mainly exhibit tackifying effect. Accordingly, rosin or ester thereof with a polyhydric alcohol like glycerin is conjointly used with rubber or plastics to produce a pressure sensitive adhesive, hotmelt adhesive and the like. Further rosin is modified into a resin having a high softening point of 120° to 180°C, by reacting it with maleic acid, fumaric acid or phenolic resin, followed by esterification with polyhydric alcohol or by converting it to a polyvalent metal salt such as calcium or zinc salt. The resin thus obtained is used widely in coating compositions, printing inks and adhesives.

However, rosin has the disadvantage as a naturally occurring material that its supply is not stable and there is no possibility of increased production.

It is therefore a matter of great importance in the art to synthesize a rosin-like resin having properties and characteristics similar to those of rosin.

A main object of the invention is accordingly to provide a novel rosin-like resin having properties and characteristics similar to those of rosin and capable of being used as substitutes for rosin as well as derivatives thereof.

Another object of the invention is to provide a process for manufacturing a rosin-like resin having the above properties and characteristics from materials easily available on a commercial scale.

Another object of the invention is to provide a composition containing a novel rosin-like resin which can be used for a wide variety of purposes as substitutes for rosin- or its derivative-containing compositions, such as emulsifiers for producing synthetic rubber by emulsion polymerization, sizing compositions, pressure sensitive adhesives, hotmelt adhesives, coating compositions, printing inks and the like.

Another object of the invention is to provide an emulsifying composition for producing synthetic rubber by emulsion polymerization, which is similar to or superior to conventional emulsifying agents containing disproportionated rosin.

Another object of the invention is to provide a sizing composition for paper, which displays more excellent sizing effect as compared not only with conventional rosin sizes but also with fortified rosin sizes.

These and other advantages and objects of the present invention will be apparent from the following description.

The resin of this invention has the following structure:

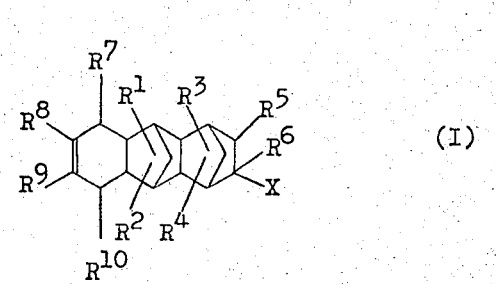

wherein each of $R^1$, $R^2$, $R^3$, $R^4$, $R^5$ and $R^6$ is hydrogen or methyl group, each of $R^7$, $R^8$, $R^9$ and $R^{10}$ is hydrogen, alkyl group having 1 to 6 carbon atoms or phenyl group and X is —CN, —CONH$_2$, —COOM or —COOR$^a$, M being hydrogen, —NH$_4$ or alkali metal, R$^a$ being alkyl group having 1 to 4 carbon atoms.

The above-mentioned structure of the present resin can be ascertained by infrared absorption spectra, nuclear magnetic resonance spectra, mass spectra, gel permeation chromatography, etc. As will be apparent from the molecular structure, the resin of this invention is similar to rosin or derivatives thereof in chemical structure in that it has one carboxyl group or a group derived therefrom and an alicyclic group containing unsaturated carbon-carbon bond. Moreover, the present resin is a resinous substance like rosin and is similar thereto in properties. Resin having 16 to 24 carbon atoms in total except for carbons contained in the group represented by X in formula (I) especially exhibits properties very similar to rosin. This resin is found to have a molecular weight of 258 to 352 by gel permeation chromatography (calculated as polystyrene) and has a theoretical acid value of 159 to 217 and a ring and ball softening point similar to that of balsam up to 100°C. Resin having 18 to 20 carbon atoms in total as described above, is the most preferable.

Thus the resin of this invention resembles rosin or the derivatives thereof in molecular structure and in properties and can be used extensively in various fields as a substitute for rosin or its derivatives.

Examples of the resin are as follows:

1. Resin represented by the formula (I) wherein X is COOM', M' being alkali metal or —NH$_4$:

This resin can be used in the form of an aqueous solution as an emulsifier for emulsion polymerization, emulsifier for wax, oil and resin emulsion and sizing agent for paper, and is especially advantageous for application as an emulsifier for synthetic rubber, since disproportionation is not necessary unlike rosin. For application as a sizing agent for paper, an improved sizing effect can be attained if the resin is used conjointly with a highly hydrophilic substance such as maleinized rosin soap as in the case of fortified rosin size. Furthermore, a water-soluble metal salt such as calcium chloride is added to the alkali salt, followed by double decomposition to obtain a metal salt, which is usable as a resin for printing ink and coating composition.

2. Resin represented by the formula (I) wherein X is a carboxyl group:

Like rosin, maleic anhydride is added to this resin with heating by addition reaction and the adduct is neutralized with alkali to obtain an alkali salt for use as a sizing agent for paper. If esterified with polyhydric alcohol, the resin is applicable to coating composition and printing ink as so-called maleic acid resin. Further if calcium hydroxide, calcium acetate, zinc oxide, magnesium hydroxide or the like is added to this resin or to a maleinized product thereof and the mixture is reacted in molten state, a resin is obtained which resembles an alkaline earth metal salt of rosin having a high softening point and which is useful for printing ink and coating composition. When the resin, as it is or after hydrogenation, is esterified with polyhydric alcohol, the resulting ester is employable for a pressure sensitive adhesive, hotmelt adhesive and the like.

3. Resin represented by the formula (I) wherein X is a nitrile group:

The X is converted to amine by catalytic reduction. Like rosin amine, this resin can be used as a polyamide modifying agent, adhesive, sterilizing agent, insecticide, antiseptic, emulsifying agent of the cation type and sizing agent of the cation type for paper making.

4. Resin represented by the formula (I) wherein X is an ester:

Interesterification of this resin with polyhydric alcohol yields a resin, which resembles ester gum for applications similar to those described above.

5. Resin represented by the formula (I) wherein X is nitrile, amide, or ester:

This resin is saponified with an alkali such as hydroxide of an alkali metal and ammonia into an alkali salt of carboxylic acid which is usable in the same manner as (1) above. Hydrolysis with acid or saponification with alkali, followed by acidification for conversion to carboxylic group assures like application as in the case of (2) above.

Thus the resin of the invention can be used in various fields as substitutes for rosin and its derivatives. It is particularly preferable to employ the present resin in the form of aqueous solution of the alkali salt thereof as sizing agent and as emulsifying agent for producing synthetic rubber by emulsion polymerization.

The resin (I) of this invention is obtained by reacting an 8-substituted tetracyclo [4,4,1$^{2.5/7.10}$0$^{1.6}$] dodecene-3 derivative represented by the formula of

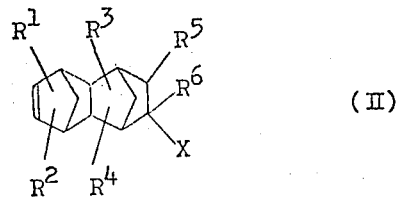

wherein $R^1$, $R^2$, $R^3$, $R^4$, $R^5$ and $R^6$ and X are the same as above with an aliphatic conjugated diene represented by the formula of

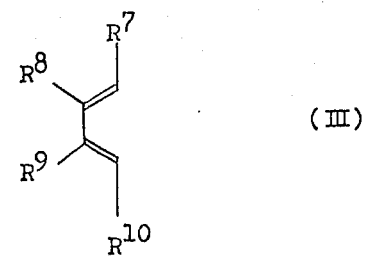

wherein $R^7$, $R^8$, $R^9$ and $R^{10}$ are the same as above to effect Diels-Alder addition reaction.

The 8-substituted tetracyclo [4,4,1$^{2.5/7.10}$ $^{01.6}$] dodecene-3 derivative (II) used as a starting material is a known compound which can be easily synthesized by reacting cyclopentadiene with an unsaturated compound, such as acrylic acid ester or acrylonitrile, which yields carboxylic acid or its salt when hydrolyzed or saponified. This reaction is disclosed, for example, by V. G. Yashunskii, A. P. Terent'ev and Ya. G. Nekhlin in "Journal of General Chemistry of U.S.S.R.," vol. 26, 831 (1956) and by A. S. Onishchenko in "Diene Synthesis". More specifically, it can be synthesized easily for instance by reacting cyclopentadiene with α,β-unsaturated carbonyl compound in the presence or absence of a solvent at an elevated temperature of 60° to 260°C, preferably of 150° to 200°C. The unsaturated carbonyl compound to be used includes compounds capable of giving carboxylic acid or its salt when hydrolyzed or saponified. Examples are alkyl ($C_1$ to $C_6$) esters, nitriles and amides of $\alpha,\beta$-unsaturated carboxylic acids such as acrylic acid, methacrylic acid, crotonic acid, etc. Cyclopentadienes to be used are cyclopentadiene and dicyclopentadiene which gives cyclopentadiene when heated for reaction. Alkyl-substituted compounds of these dienes are also employable. These cyclopentadienes are easily available in large amounts from the petrochemical industry. The 8-substituted tetracyclo $[4,4,1,^{2.5/7.10}0^{1.6}]$ dodecene-3 derivative (II) obtained by the foregoing reaction can be separated from the reaction mixture by distilling off unreacted substances. It is preferable to remove by-products, if any. The resulting product or carboxylic acid or its salt obtained by saponifying the product with acid or alkali is used as a starting material for producing the resin of this invention.

The aliphatic conjugated diene (III), the other starting material, includes chain hydrocarbons having conjugated double bond in the molecule. Examples to be used are butadiene, isoprene, piperylene, 2,4-hexadiene, 2-methyl-1,3-pentadiene, 3-methyl-1,3-pentadiene, 4-methyl-1,3-pentadiene, 2-ethylbutadiene, 2,3-dimethyl-1,3-butadiene, 2-isopropyl-1,3-pentadiene, 1,1,3-trimethyl-1,3-butadiene, 2,4-octadiene, 2,5,5-trimethyl-1,3-hexadiene, 2-n-amyl-1,3-butadiene, 2-t-butyl-1,3-butadiene, 2-phenyl-1,3-butadiene, etc.

The 8-substituted tetracyclo $[4,4,1,^{2.5/7.10}0^{1.6}]$ dodecene-3 derivative (II) and aliphatic conjugated diene (III) are subjected to addition reaction of the Diels-Alder type within a sealed or open reaction vessel in the presence or absence of solvent. For instance, the reaction system can be subjected to Diels-Alder reaction by heating the same to 50° to 260°C. The starting materials are preferably used in such ratio that at least 1 mole of the latter (III) is used per mole of the former (II). For reaction, both may be charged in the reactor at the same time, or 8-substituted tetracyclo $[4,4,1,^{2.5/7.10}\ 0^{1.6}]$ dodecene-3 derivative (II) is first placed in the reactor and aliphatic conjugated diene (III) is then added thereto. The latter method is especially advantageous when the reaction is conducted at a high temperature. Although the reaction proceeds in the air, it is advantageous to conduct the reaction in an inert gas atmosphere, since side reaction can be inhibited to obtain a resin of light color. Undesirable polymerization of the conjugated diene (III) with itself can be prevented by using a radical polymerization inhibitor or a chain transfer inducing agent. Generally, the reaction is completed in about 1 to 20 hours, although the reaction time varies depending on the reaction conditions. Thus resin having the structure of the formula (I) is obtained.

The resin of the formula (I) wherein X is nitrile group, amide group or ester group can be hydrolyzed or saponified with acid or alkali into carboxylic acid or its alkali salt. The resin containing free carboxyl group is neutralized with alkali to produce alkali salt thereof. The hydrolysis or saponification is conducted under the conditions and in the manner already known. The alkali to be used are, for example, lithium hydroxide, sodium hydroxide, potassium hydroxide, ammonia, etc.

As hereinafter disclosed, a composition containing the present resin having the formula (I) before can be used in various fields as a substitute for rosin and its derivatives. Particularly, composition comprising aqueous medium and an alkali salt of the resin (I) dispersed therein is useful as an emulsifying composition for producing synthetic rubber by emulsion polymerization and as a sizing agent for paper. The alkali salts of the resin (I) include, for example, lithium, sodium, potassium, ammonium salts of the resin (I).

The emulsifying composition of the invention is in the form of aqueous dispersion containing the resin (I) dispersed in water and is applicable to produce various synthetic rubbers by emulsion polymerization, examples of the synthetic rubbers being styrene-butadiene rubber, acrylonitrile rubber, chloroprene rubber, polybutadiene rubber, acrylonitrile-butadiene rubber, etc. The resin (I) has a good water-solubility at low temperature and the aqueous dispersion thereof is excellent in storage stability at low temperature, so that the emulsifying composition containing the same can be effectively used for producing cold rubber. Further, the resin (I) has a property to impart tackiness to synthetic rubbers, which is superior to that of rosin soaps and, therefore, synthetic rubbers having excellent amenability to processing can be obtained using the present emulsifying composition. Further, the present emulsifying composition is light in color and excellent in thermal and weather resistances, so that when it is used in emulsion polymerization synthetic rubbers having light color and excellent thermal and weather resistances are obtainable. According to the emulsifying composition of the invention, moreover, it is possible to produce synthetic rubber having high order of polymerization degree in a high yield.

The emulsifying composition of the invention can be used as an emulsifying agent for producing synthetic rubber by emulsion polymerization in the same manner as known emulsifying agent of this kind, e.g., rosin soap. It may be employed alone or in combination with various conventional emulsifying agents of this kind such as fatty acid soaps, synthetic surfactants, rosin soaps, etc.

The sizing composition of the invention is also employed in the form of aqueous dispersion of alkali salt of the resin (I). Whereas conventional sizing agents containing modified petroleum resins require the addition of rosin in admixture therewith, the sizing agent of this invention exhibits a high sizing effect comparable to the fortified rosin size, without using rosin. However, rosin can be incorporated in the sizing composition of this invention. Especially when an addition product of rosin with $\alpha,\beta$-unsaturated polybasic acid is added to the sizing agent of this invention up to an amount of 30 wt.% based on the total solid contained in the composition, an outstanding sizing effect can be achieved which is much greater than the effect produced by the fortified rosin size. Moreover, the sizing agent of this invention has excellent stability during storage.

Further, as will be presumable from the foregoing formula, the sizing resin of this invention has a close resemblance to rosin in properties. For instance, it is of a suitable balance (HLB) between its hydrophobic group and hydrophilic group and has a contact angle in the range of 70° to 100° which covers the contact angle of rosin ranging from 80° to 85°. Presumably, these characteristics permit the present sizing agent to have good water-dispersibility and to give a very high sizing effect without the necessity to incorporate rosin therein. In addition, the present sizing agent has good stability against acids, and especially when used as a surface sizing agent, it is free of gumming up. It is noted that in any method of surface sizing, the contact of the sizing agent with paper causes a acidic substance in the paper such as aluminum sulfate to penetrate into the sizing agent, whereupon the sizing agent, if it is poor in acid stability, will react with the acidic substance, permitting the resin component to precipitate in the form of a water-insoluble metal salt or producing a free resin component which undergoes coagulation of resin component of the sizing agent, consequently stains the roll or blanket or produces spots on the paper or like objectionable results. The sizing agent of this invention is free of such deficiency.

The sizing agent of the present invention can be used in the same manner as conventional sizing agents of the rosin or petroleum resin type, by internal addition as well as by surface sizing. It may be used conjointly with a well-known sizing agent designed for internal addition or for surface sizing, such as rosin size, fortified rosin size, petroleum resin size, starch, protein, polyvinyl alcohol or the like.

The properties of the present resin (I) can further be improved by hydrogenation thereof. The hydrogenation process can be conducted in the same manner as known in the art. For example, before or after the hydrolysis the resin (I) is placed in a pressure container such as an autoclave in the form of solvent solution or of molten state. Examples of the solvent are benzene, toluene, xylene, isohexane, cyclohexane and like hydrocarbons. Thereafter, the resin (I) is brought into contact with hydrogen gas in the presence of a catalyst at 10° to 500 kg/cm² of hydrogen pressure at 150° to 300°C. Employable as catalysts are, for example, metals such as nickel, cobalt, molybdenum, paladium, copper, chromium, ruthenium, etc. and oxides thereof.

When a composition containing an alkali salt of such hydrogenated resin dispersed in water is used as an emulsifier for producing synthetic rubber, the resultant rubber has lighter color and more excellent thermal and weather resistance.

Examples of this invention are given below for a better understanding of the invention, in which all percentages are by weight. The drawings referred to in examples are as follows.

EXAMPLE 1

In a one-liter autoclave were placed 182 g of dicyclopentadiene, 73 g of acrylonitrile and 150 g of xylene. After the air in the autoclave was replaced with nitrogen the mixture was heated at 220°C for 3 hours. The resultant reaction mixture was subjected to distillation under reduced pressure to remove unreacted substances, solvents and low boiling distillation. Desired product was obtained by further distillation at 120° to 150°C at a reduced pressure of 5 mm Hg. The product was found to have a molecular weight of about 190 and to contain at least 95% of 8-cyanotetracyclo [4,4,1,$^{2.5/7.10}0^{1.6}$]-dodecene-3 having the following formula by gel permeation chromatography and by infrared spectrum of the principal component separated by a fraction collector associated with gel permeation chromatography.

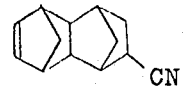

Into a flask equipped with a stirrer, reflux condenser, dropping funnel and thermometer was placed 37 g of 8-cyanotetracyclo [4,4,1,$^{2.5/7.10}0^{1.6}$]dodecene-3 thus obtained and the air was replaced with nitrogen. The compound was heated to 170°C and, while keeping this temperature, 13.6 g of isoprene was added dropwise to the material over a period of 10 hours. After completion of the dropwise addition, the reaction mixture was distilled at 150°C at a reduced pressure of 5 mm Hg to remove unreacted substances, whereby 29 g of a resinous product was obtained.

Figure 1:
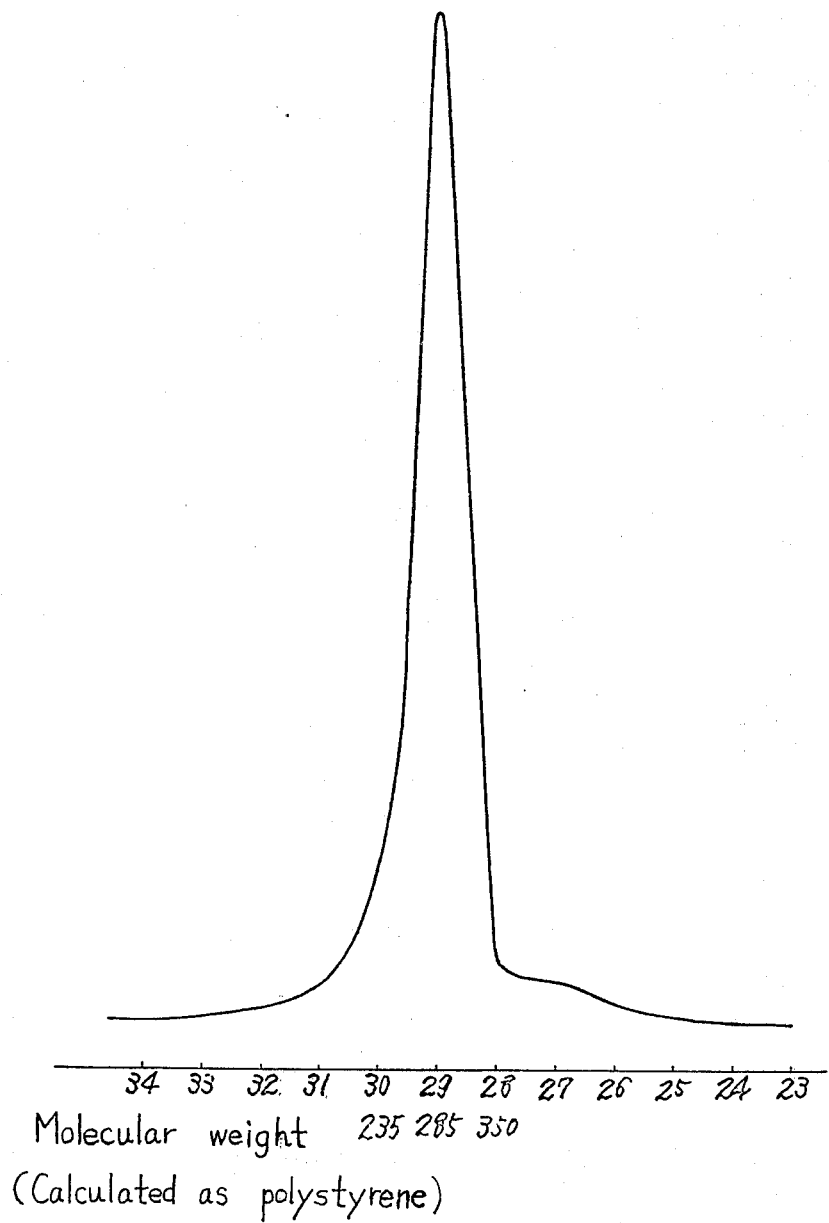
FIG. 1 shows the gel permeation chromatography of the resin according to Example 1.

20 g of this resin and 85 g of 10% aqueous solution of KOH were placed into an autoclave and hydrolyzed at 200°C for 2 hours. The reaction mixture obtained was acidified with hydrochloric acid, followed by addition of toluene to extract a resin component. Removal of toluene from the toluene layer gave 19 g of light yellow resin, which had a molecular weight of 278, acid value of 192 and softening point of 77.5°C. Gel permeation chromatography, mass spectrum, infrared absorption spectrum and nuclear magnetic resonance spectrum were measured respectively. For gel permeation chromatography, the resin obtained as above was used as a sample. Resin purified by a fraction collector associated with gel permeation chromatography was used for the measurement of infrared absorption spectrum, and methyl ester of the purified product was used for the determination of nuclear magnetic resonance absorption. The result of measurement of gel permeation chromatography are shown in FIG. 1, that of infrared absorption spectrum in FIG. 2 and that of nuclear magnetic resonance spectrum in FIG. 3. These results indicate that the resin obtained principally comprises a mixture of two isomers (theoretical molecular weight: 272, theoretical acid value: 206) of the formula

EXAMPLE 2

Into a 500-ml autoclave were placed 66 g of cyclopentadiene, 43 g of methyl acrylate and 109 g of xylene, with the air replaced with nitrogen. The mixture was then heated at 200°C to effect reaction for 3 hours. After cooling, the reaction mixture was distilled at 150°C at a reduced pressure of 5 mm Hg to remove unreacted substances, solvent and low boiling distillate, whereby 71 g of a resinous product was obtained. The results of gel permeation chromatography of the resinous product and infrared spectrum of the principal component separated by a fraction collector associated with gel permeation chromatography indicate that the product contains at least 80% of 8methoxycarbonyltetracyclo[4,4,1,$^{2.5/7.10}0^{1.6}$]dodecene-3 of

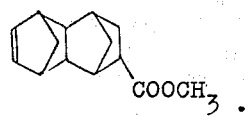

Into a one-liter autoclave equipped with a metering pump were placed 109 g of 8-methoxycarbonyltetracyclo[4,4,1,$^{2.5/7.10}0^{1.6}$]dodecene-3 and 109 g of xylene, with the air replaced with nitrogen. The mixture was then heated to 200°C and, while keeping the same temperature, 27 g of butadiene was poured into the autoclave through the metering pump over a period of two hours. The same temperature was further maintained for 1 hour and the mixture was then cooled and distilled at 150°C under reduced pressure of 5 mm Hg to remove unreacted substances and solvent, whereby 80 g of a resinous product was obtained. 50 g of the resinous product was placed in a flask and heated to 120° to 130°C. 19.0 g of 48% aqueous solution of KOH was then added dropwise to the product with stirring over a period of 1 hour. The mixture was further kept at the same temperature for hydrolysis. After cooling, the reaction mixture was acidified with hydrochloric acid, and a resin component was extracted with toluene. Removal of toluene from the toluene layer gave 35 g of light yellow resin, which had a molecular weight of 263, acid value of 205 and softening point of 88°C. The resin was subjected to gel permeation chomatography and further to the measurement of mass spectrum, infrared absorption spectrum and nuclear magnetic resonance absorption in the same manner as in Example 1. The results indicate that the resin chiefly comprises a compound of the formula

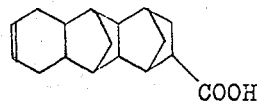

Figure 4:
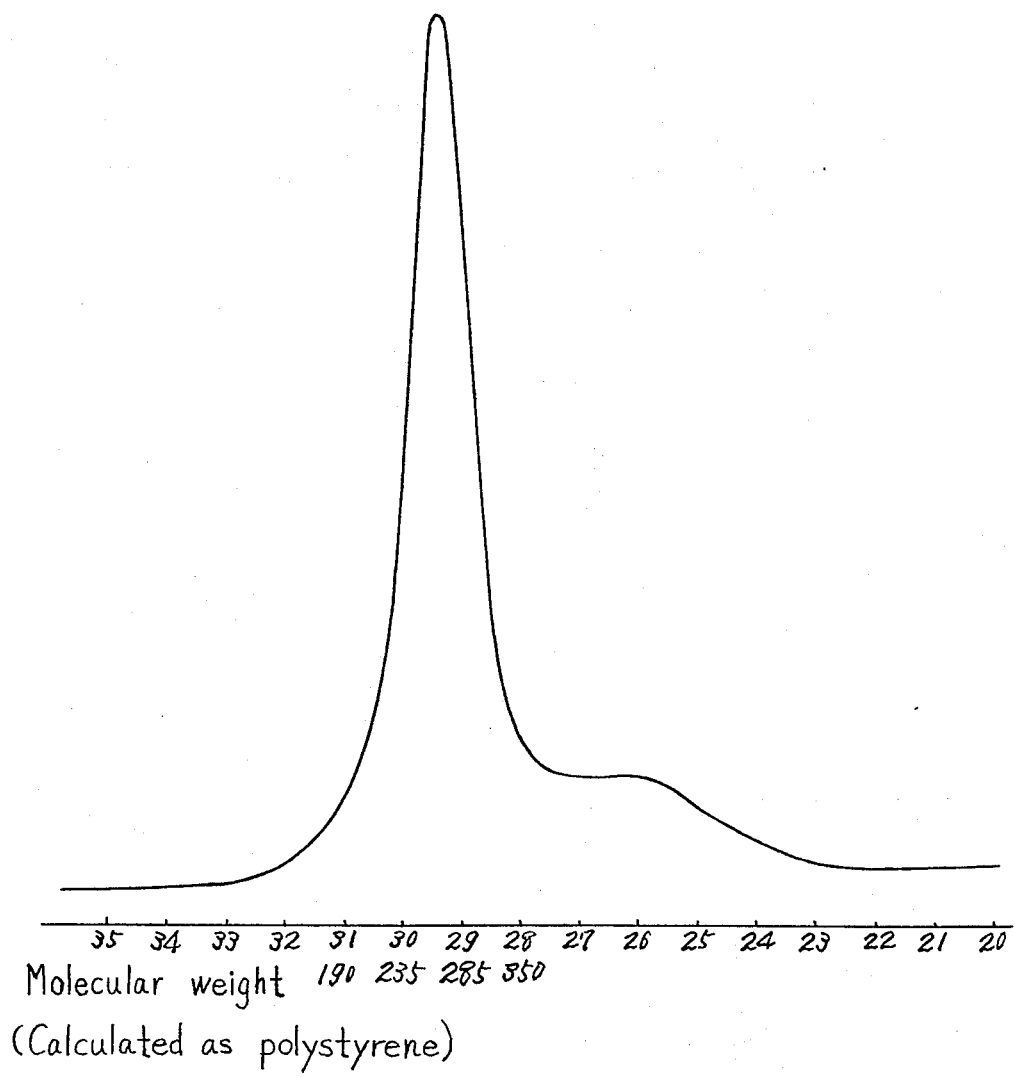
FIG. 4 shows the gel permeation chromatography of the resin according to Example 2.

FIG. 4 shows the results of gel permeation chromatography.

EXAMPLE 3

Figure 2:
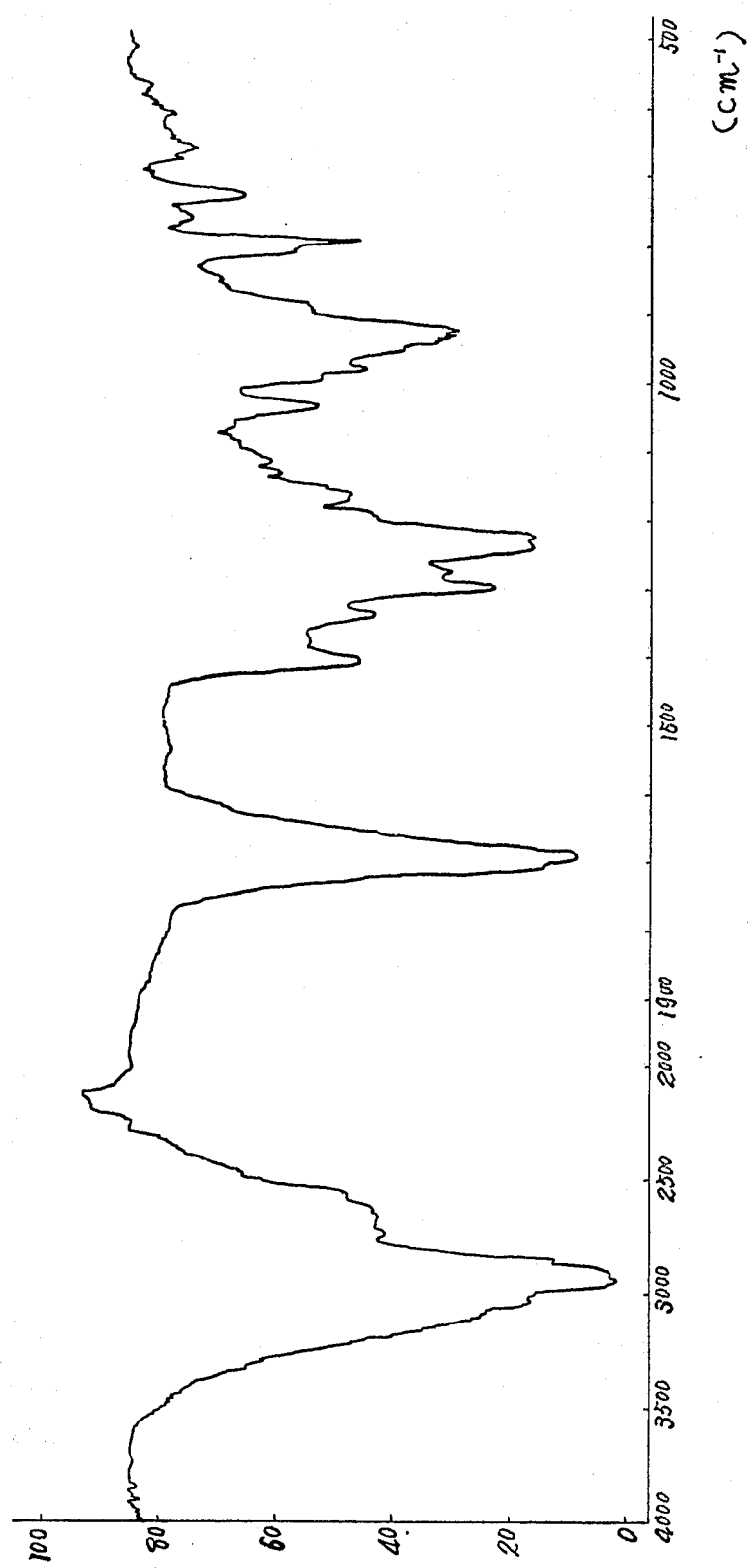
FIG. 2 shows the infrared absorption spectrum of the same resin.
Figure 3:
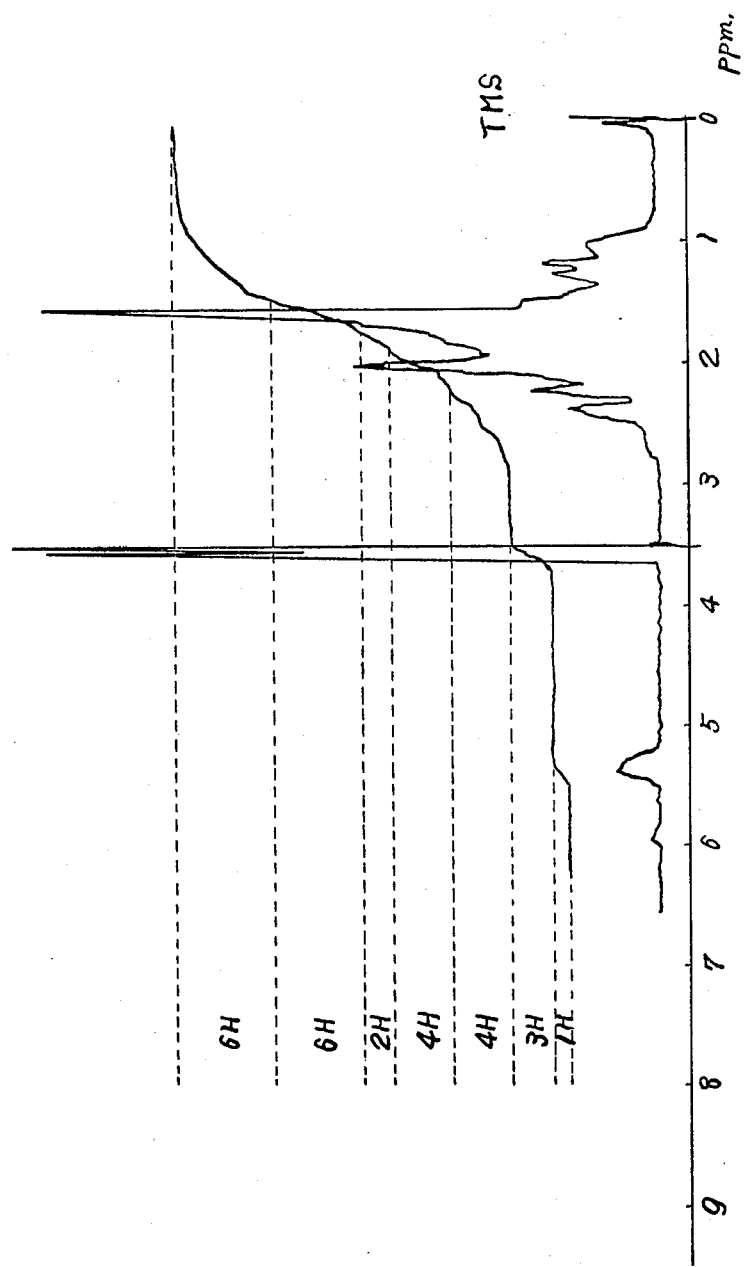
FIG. 3 shows the nuclear magnetic resonance spectrum of the same resin.

71 g of 8-methoxycarbonyl-tetracyclo[4,4,1,$^{2.5/7.10}0^{1.6}$]dodecene-3 obtained in the same manner as in Example 2, 71 g of xylene, 0.3 g of hydroquinone monomethylether and 22.4 g of isoprene were placed into an autoclave, with the air replaced with nitrogen. The mixture was then heated to 200°C to effect reaction for 3 hours. After cooling, the reaction mixture was distilled at 150°C at a reduced pressure of 5 mm Hg to remove unreacted substances and solvent, whereby 45 g of resinous product was obtained. The resinous product and 18.5 g of 48% aqueous solution of KOH were placed into a flask to conduct hydrolysis and extraction with toluene in the same manner as in Example 2, whereby 40.7 g of light yellow resin was obtained. The resin had an average molecular weight of 278, acid value of 197 and softening point of 78°C. The resin was further subjected to gel permeation chromatography and to the measurement of infrared absorption spectrum, nuclear magnetic resonance spectrum and mass spectrum. The results were exactly identical to those obtained in Example 1 as shown in FIG. 1, 2 and 3. Thus the principal component of the resin was found to be a mixtures of two isomers having the formulas of

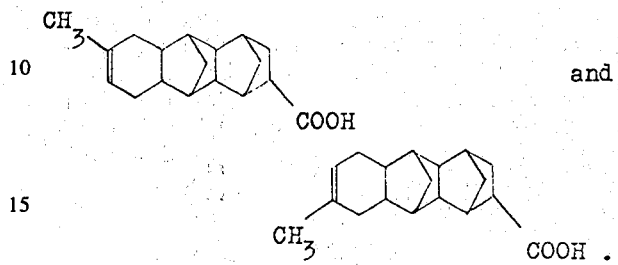

EXAMPLES 4 and 5

The same procedures as in Example 3 were followed to obtain resinous products using 50 g of 8-methoxycarbonyl-tetracyclo[4,4,1,$^{2.5/7.10}0^{1.6}$]-dodecene-3 prepared in the same manner as in Example 2, except that specified amounts of 1,3-pentadiene and 2,4-hexadiene were used in place of isoprene. The results are given in Table 1.

Table 1

| | Example 4 | Example 5 |
|---|---|---|
| Aliphatic conjugated diene | | |
| Kind | Cis-1,3-pentadiene | 2,4-hexadiene |
| Amount used (g) | 15.6 | 18.8 |
| Yield of resin | | |
| Before hydrolysis (g) | 30.8 | 24.8 |
| After hydrolysis (g) | 27.6 | 20.6 |
| Properties of resulting resin | | |
| Molecular weight | 278 | 300 |
| Acid value | 196 | 188 |
| Softening point (°C) | 80 | 75 |

Each of the resins obtained was subjected to gel permeation chromatography and to the measurement of mass spectrum, infrared absorption spectrum and nuclear magnetic resonance spectrum. The test results indicate that the resin of Example 4 principally comprises a mixture of two isomers having the formulas of

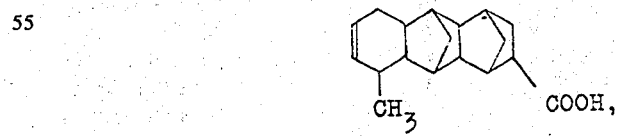

and that the resin of Example 5 principally comprises

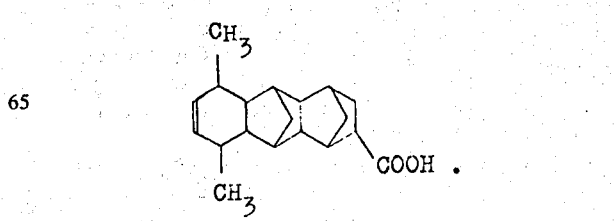

Figure 5:
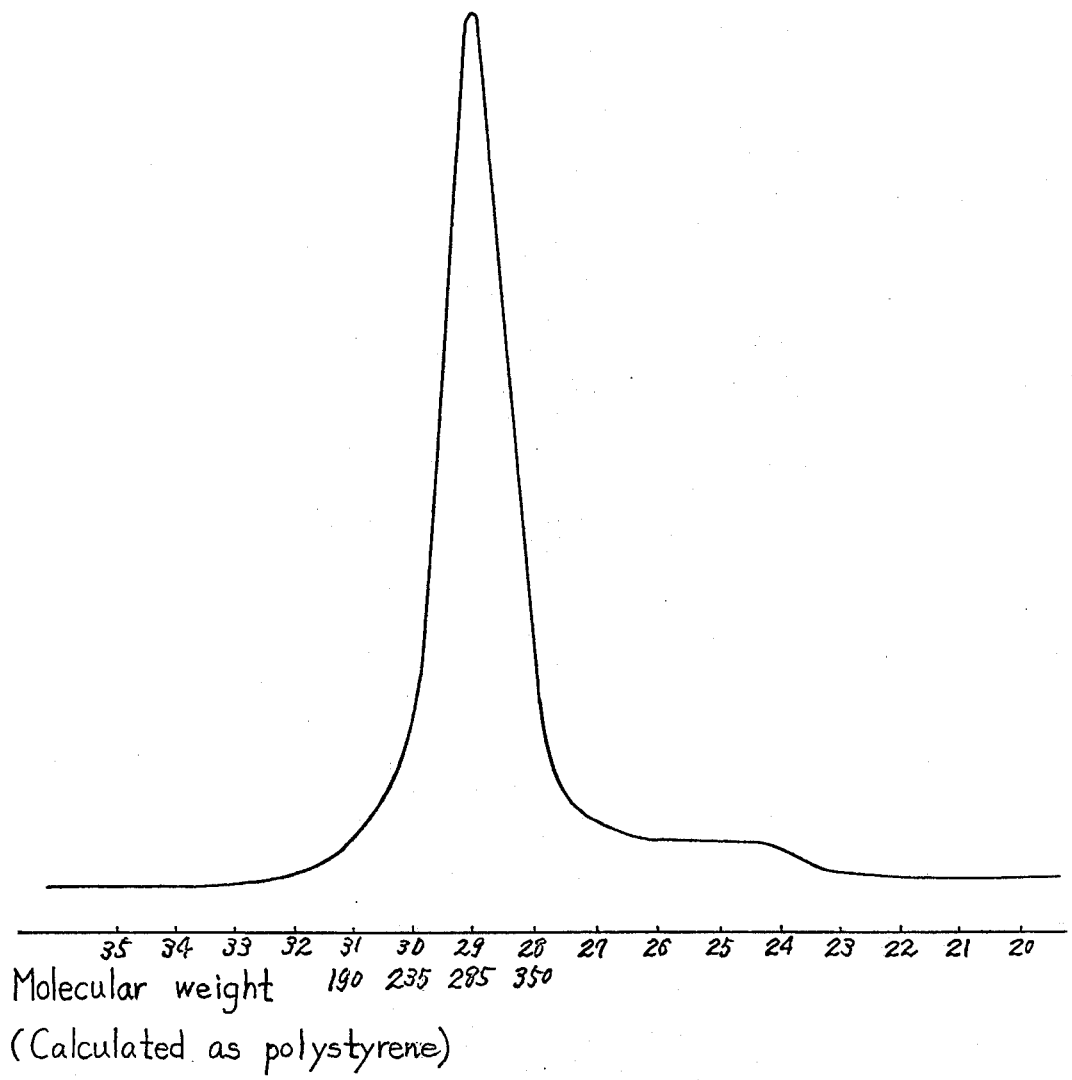
FIG. 5 shows the gel permeation chromatography of the resin according to Example 4.
Figure 6:
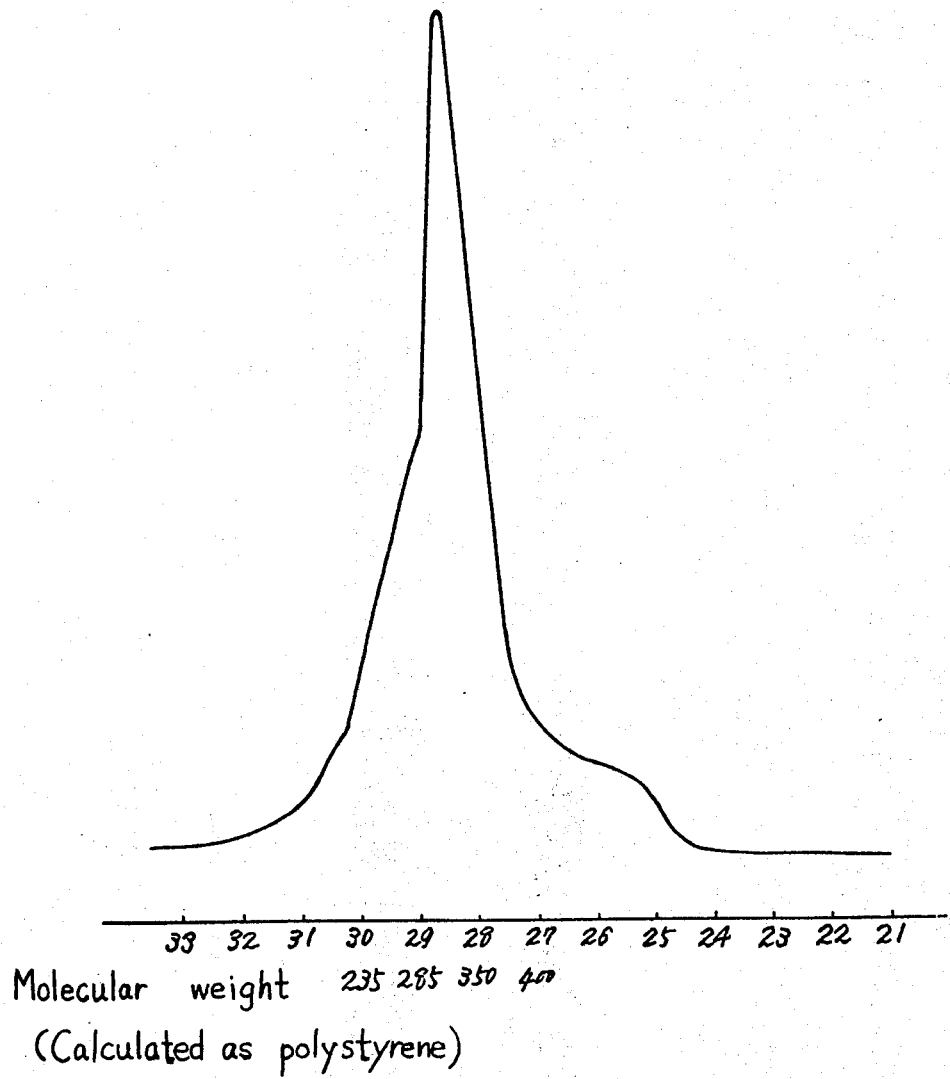
FIG. 6 shows the gel permeation chromatography of the resin according to Example 5.

The results of gel permeation chromatography of these resins are shown in FIGS. 5 and 6 respectively.

EXAMPLE 6

In 100 g of cyclohexane was dissolved 100 g of the resin obtained by the method disclosed in Example 3, to which was added 0.5 g of stabilized nickel as a catalyst. The mixture was then placed in a 500-ml autoclave and hydrogenated at 200 kg/cm$^2$ of hydrogen pressure at 270°C for 3 hours. After cooling, the reaction mixture taken out from the autoclave was filtered to separate the catalyst used. Removal of the solvent by distillation under reduced pressure gave a hydrogenated resin having a molecular weight of 300 and saponification value of 190.

EXAMPLE 7

50 g of the resinous product obtained in Example 3 was mixed, prior to saponification thereof, with 12 g of a 4 : 1 weight ratio addition product of rosin and maleic anhydride. The mixture was then saponified at 95 to 100°C with 36.8 g of 38% aqueous solution of potassium hydroxide added dropwise thereto. The resultant product was diluted with water to produce aqueous composition having a concentration of 30%.

COMPARATIVE EXAMPLE

In an autoclave were placed 193 g of dicyclopentadiene, 53 g of acrylonitrile and 246 g of xylene. The air in the autoclave was replaced with nitrogen and then the mixture was heated at 240°C for 2 hours. After cooling, the reaction mixture was subjected to distillation conducted at 150°C under a reduced pressure of 5 mm Hg to produce 135 g of a resinous substance.

Table 2 shows the properties of the resins obtained in Examples 1 to 6 in comparison with those of rosin.

95° to 100°C aqueous solution of potassium hydroxide in amounts equivalent to acid values of the resins. The resultant products were diluted with water to produce 7 kinds of aqueous compositions having concentration of 25%. Each composition was used as an emulsifier for emulsion polymerization according to cold rubber sulfoxylate formulation to obtain SBR. The conversion and stability of latex are respectively shown in Tables 4 and 5. Formulation for polymerization Table 3

| Materials used | Names of materials used | Proportions parts by weight |
|---|---|---|
| Monomer | Butadiene | 70 |
| | Styrene | 30 |
| Dispersing medium | Deionized water (degassed) | 200 |
| Emulsifier | Aqueous solution of resin of Examples (as solid) | 4.0 |
| | Napthalene-formaldehyde resin sodium sulfonate | 0.15 |
| Molecular weight adjusting agent | Tertiary dodecylmercaptan | 0.245 |
| Polymerization initiator | | |
| Oxidizing agent | p-Menthane hydroperoxide | 0.104 |
| Reducing agent | Ferrous sulfate (heptahydrate) | 0.05 |
| Secondary reducing agent | Sodium formaldehyde sulfoxylate | 0.15 |
| Chelating agent | EDTA - 4Na | 0.07 |
| Electrolyte | Sodium phosphate (dodecahydrate) | 0.8 |

Polymerization conditions
Polymerization temperature : 5°C.
Reaction time : 6 hours.
In nitrogen atmosphere.

Table 2

| Resin | Molecular weight | Acid value | Softening point | Solubility in benzene | Contact angle(degree) | Water-solubility of alkali salt |
|---|---|---|---|---|---|---|
| Rosin | 300 | 167 | 78 | Completely soluble mutually | 83 | Clear |
| Example 1 | 272 | 192 | 77.5 | " | 82 | " |
| Example 2 | 263 | 205 | 88 | " | 84 | " |
| Example 3 | 278 | 192 | 77.5 | " | 82 | " |
| Example 4 | 278 | 196 | 80 | " | 76 | " |
| Example 5 | 300 | 188 | 75 | " | 93 | " |
| Example 6 | 274 | 195 | 74 | " | 83 | " |
| Comparative Example | 204 | 174 | 120–125 (mp) | " | 62 | " |

The molecular weight in the table was determined by gel permeation chromatography (calculated as polystyrene), and the softening point by ring and ball test. The solubility in benzene was determined by inspecting the apprearance, using 10% benzene solution. The contact angle was determined by goniometric method for measuring contact angle, while the water-solubility of alkali salt was determined according to solubility in 25% aqueous solution of KOH.

The foregoing results show that the resins of this invention have properties similar to those of rosin.

The resins of this invention were tested in respect of its application as a sizing agent and emulsifier for emulsion polymerization of synthetic rubber according to the following methods, with the results given below.
1. Emulsifying composition
To the resins obtained in Examples 1 to 6 and Comparison Example was respectively added dropwise at Conversion
Table 4 gives conversion, in which is also shown that obtained in exactly the same manner as above, using a commercial disproportionated rosin emulsifier.

Table 4

| Emulsifier | Conversion (%) |
|---|---|
| Example 1 | 61.1 |
| Example 2 | 60.8 |
| Example 3 | 63.0 |
| Example 4 | 60.3 |
| Example 5 | 62.1 |
| Example 6 | 63.2 |
| Commercial disproportionated rosin emulsifier | 61.7 |

Stability test of latex
50 g of 25% aqueous solution of the latex obtained in the above polymerization system was placed in a container and subjected to mechanical shearing force at a temperature of 25°C for 5 minutes, under a load of 5 kg and at a rotational speed of 1000 r.p.m. The resulting coagulation was filtered by an 80-mesh stainless screen and dried to determine the rate of the coagulation formed.

$$\text{Rate of coagulation formed (\%)} = \frac{\text{Weight of coagulation dried completely}}{12.5} \times 100$$

The smaller the rate of coagulation formed, the more stable is the latex.

Table 5 shows the result in comparison with that obtained with the use of the commercial disproportionated rosin emulsifier.

Table 5

| Emulsifier | Rate of coagulation formed (%) |
|---|---|
| Example 1 | 1.54 |
| Example 2 | 1.62 |
| Example 3 | 1.47 |
| Example 4 | 1.58 |
| Example 5 | 1.48 |
| Example 6 | 1.42 |
| Commercial disproportionated rosin emulsifier | 1.50 |

2. Sizing Composition

To the resins obtained in Example 1 to 5 and Comparison Example was respectively added dropwise at 95° to 100°C aqueous solution of potassium hydroxide in amounts equivalent to acid values of the resins. The resultant products were diluted with water to produce 6 kinds of aqueous compositions having concentration of 30%.

The above compositions and the composition obtained in Example 7 were respectively subjected to the following tests to determine stability for storage and for acid and sizing effect.

A. Stability for storage

Each composition was diluted with water to a concentration of 5% and left to stand at room temperature. The change of the composition was evaluated with the unaided eye. The results are shown in Table 6 below.

B. Stability for acid

Each composition was diluted with water to a concentration of 5% and 0.5 ml of the diluted composition was mixed with 500 ml of distilled water. Thereafter, 2.5 ml of 5% aqueous solution of aluminum sulfate was added to the mixture with stirring, the pH of the resultant mixture being 4.5±0.1. The mixture was left to stand for observation. The results are shown in Table 6 below.

C. Sizing effect

Each composition was added to L-BKP, having a beating degree of 30.5°SR and adjusted to a concentration of 1 wt.%, in an amount of 0.5% based on the pulp and calculated as solids. After agitation, an aqueous solution of aluminum sulfate was further added to the pulp in a relative amount of 2.5 wt.% as above and the mixture was thoroughly agitated. The resulting stock was made into a sheet on a TAPPI standard sheet machine and dried at 80°C for 5 minutes. Sizing effect was tested on the resulting paper web, weighing 60±1 g/m² by Stockight method with the results shown in Table 7.

Table 6

| Composition | Stability for storage | | | Stability for acid |
|---|---|---|---|---|
| | Immediately after preparation | 10 days after preparation | One month after preparation | |
| Example 1 | Transparent | Transparent | Transparent | Minute flocks in 5 hrs. |
| Example 2 | " | " | " | " |
| Example 3 | " | " | " | Minute flocks in 7 hrs. |
| Example 4 | " | " | Slightly turbid | Minute flocks in 4 hrs. |
| Example 5 | " | " | " | " |
| Example 7 | " | " | Transparent | Minute flocks in 3.5 hrs. |
| Comparison Example | " | Precipitation | Marked precipitation | Immediate flocculation, followed by precipitation in 1 hr. |

Table 7

| Composition | Sizing effect (sec.) |
|---|---|
| Example 1 | 28 |
| Example 2 | 24 |
| Example 3 | 29 |
| Example 4 | 26 |
| Example 5 | 28 |
| Example 7 | 33 |
| Comparison Example | 15 |
| Rosin size | 18 |
| Fortified rosin size | 29 |

What we claim is:

1. A resin having a formula of

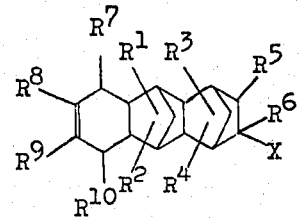

wherein each of $R^1$, $R^2$, $R^3$, $R^4$, $R^5$ and $R^6$ is hydrogen or methyl group, each of $R^7$, $R^8$, $R^9$ and $R^{10}$ is hydrogen, alkyl group having 1 to 6 carbon atoms or phenyl group and X is —CN or CONH$_2$—.

2. A composition which comprises an aqueous medium and a resin dispersed therein, said resin having the formula of

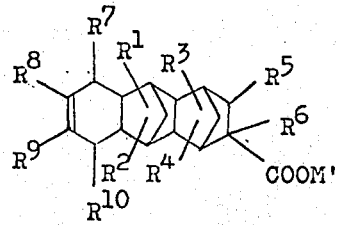

wherein each of $R^1$, $R^2$, $R^3$, $R^4$, $R^5$ and $R^6$ is hydrogen or methyl group, each of $R^7$, $R^8$, $R^9$ and $R^{10}$ is hydrogen, alkyl group having 1 to 6 carbon atoms or phenyl group and M' is —NH$_4$ or alkali metal.

3. An emulsifying composition for producing a synthetic rubber by emulsion polymerization which comprises aqueous medium and a resin dispersed therein, said resin having the formula of

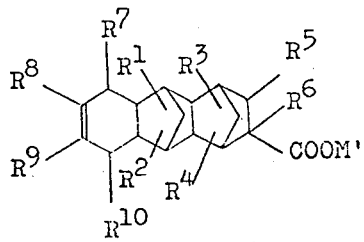

wherein each of $R^1$, $R^2$, $R^3$, $R^4$ $R^5$ and $R^6$ is hydrogen or methyl group, each of $R^7$, $R^8$, $R^9$ and $R^{10}$ is hydrogen, alkyl group having 1 to 6 carbon atoms or phenyl group and $M'$ is $-NH_4$ or alkali metal.

4. A sizing composition for paper which comprises an aqueous medium and a resin dispersed therein, said resin having the formula of

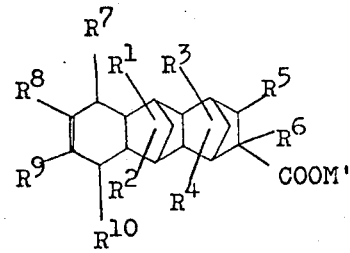

wherein each of $R^1$, $R^2$, $R^3$, $R^4$, $R^5$ and $R^6$ is hydrogen or methyl group, each of $R^7$, $R^8$, $R^9$ and $R^{10}$ is hydrogen, alkyl group having 1 to 6 carbon atoms or phenyl group and $M'$ is $-NH_4$ or alkali metal.

* * * * *